(12) United States Patent
Kirsch

(10) Patent No.: US 7,066,934 B2
(45) Date of Patent: Jun. 27, 2006

(54) ADHESIVE INCLUDING MEDICAMENT AND DEVICE AND METHOD FOR APPLYING SAME

(75) Inventor: Wolff M. Kirsch, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 695 days.

(21) Appl. No.: 10/032,225

(22) Filed: Dec. 18, 2001

(65) Prior Publication Data

US 2003/0050590 A1 Mar. 13, 2003

Related U.S. Application Data

(60) Provisional application No. 60/306,572, filed on Jul. 19, 2001, provisional application No. 60/308,993, filed on Jul. 31, 2001, provisional application No. 60/337,662, filed on Nov. 7, 2001, and provisional application No. 60/341,598, filed on Dec. 17, 2001.

(51) Int. Cl.
*A61F 13/00* (2006.01)
*A61B 17/08* (2006.01)

(52) U.S. Cl. .......................... 606/41; 602/52; 606/214; 606/215; 606/216

(58) Field of Classification Search ......... 602/213–216, 602/41–59; 606/213–216; 604/304–306
See application file for complete search history.

(56) References Cited

U.S. PATENT DOCUMENTS

| | | | |
|---|---|---|---|
| 3,483,870 A | | 12/1969 | Coover et al. |
| 3,668,050 A | * | 6/1972 | Donnelly ................... 128/849 |
| 3,971,766 A | * | 7/1976 | Ono et al. ............. 526/318.41 |
| 4,057,535 A | * | 11/1977 | Lipatova et al. ............... 528/68 |
| 4,616,642 A | * | 10/1986 | Martin et al. ................ 128/853 |
| 5,556,375 A | | 9/1996 | Ewall |
| 5,569,223 A | | 10/1996 | Wandell et al. |
| 5,632,727 A | | 5/1997 | Tipton et al. |
| 5,684,042 A | | 11/1997 | Greff et al. |
| 5,811,091 A | | 9/1998 | Greff et al. |
| 6,155,265 A | | 12/2000 | Hammerslag et al. |
| 6,410,818 B1 | * | 6/2002 | Oyaski ........................ 602/54 |

FOREIGN PATENT DOCUMENTS

| | | |
|---|---|---|
| EP | 0028452 A | 5/1981 |
| FR | 2574285 A | 6/1986 |
| GB | 2202150 A | 9/1988 |
| WO | WO 96 00760 A | 1/1996 |
| WO | WO 96 10374 A | 4/1996 |
| WO | WO 99 30685 A | 6/1999 |
| WO | WO 99 42535 A | 8/1999 |

OTHER PUBLICATIONS

International Search Report for PCT Application PCT/US 02/23221.
*Brumit, *Adhesives Age*, Feb. 1975, pp 17–22.
*Arshady, *Polymer Engineering and Science*, Dec. 1989, vol. 29, No. 24, 1746–1758.
*The American Journal of Emergency Medicine, May 2001, vol. 19, No. 3, "Foreign Body Reactions to Dermabond".
*Marx, et al., "The Development of Rapamycin and Its Application to Stent Restenosis" Circulation, 2001, 104: 852–855.
*Sousa, et al, "Sustained Suppression of Neointimal Proliferation by Sirolimus–Eluting Stents" Circulation, 2001, 104: 2007–2011.
*Bernard, et al., Arch Demeratol., Sep. 2001; 137 (9): 1177–80.
Dermabond® Topical Skin Adhesive (manufactured for Ethicon, Inc. by Closure Medical Corp.), © Ethicon, Inc. 1998.

* cited by examiner

*Primary Examiner*—Kim M. Lewis
(74) *Attorney, Agent, or Firm*—Knobbe Martens Olson & Bear LLP

(57) ABSTRACT

The present invention provides a device and method for safely applying cyanoacrylate or other adhesives to skin lacerations.

25 Claims, 6 Drawing Sheets

ADHESIVE INCLUDING MEDICAMENT AND DEVICE AND METHOD FOR APPLYING SAME

This application claims priority under 35 U.S.C. §119(e) to the following U.S. provisional applications: Ser. No. 60/306,572, filed Jul. 19, 2001, Ser. No. 60/308,993, filed Jul. 31, 2001, Ser. No. 60/307,662, filed Nov. 7, 2001, and Ser. No. 60/341,598, filed Dec. 17, 2001, the disclosures of which are hereby incorporated by reference in their entireties.

FIELD OF THE INVENTION

The present invention provides a device and method for safely applying cyanoacrylate or other adhesives to skin lacerations.

BACKGROUND OF THE INVENTION

Wound closure technology continues to evolve with non-suture alternatives such as staples, surgical tapes, and most recently, tissue adhesives, which have rapidly gained recognition and acceptance as effective wound closure methods. Two different forms of tissue adhesives for wound closure have been extensively studied: cyanoacrylate tissue adhesives and fibrin sealants. Fibrin sealants have not gained acceptance because of the low tensile strength of the fibrin polymer, lengthy preparation time, and the risk of viral transmission. The cyanoacrylates are recognized as superior adhesives for skin wound closure and are undergoing continuous modification to improve the technology.

A common property of all of the cyanoacrylates is the ability to bond and polymerize in the presence of water and to form a bond between the two sides of a wound to hold it in position. When used for wound closure, the cyanoacrylate polymerizes in the presence of water molecules on the skin surface, forming a bridge and bond that keeps the tissue together for the purpose of wound healing. The polymerized material then progressively and slowly flakes off after holding the skin tissues in that position. The difficulties and hazards associated with the use of cyanoacrylates are well known. Entry of cyanoacrylates into the wound promotes infection and a foreign body reaction. The cyanoacrylates are toxic and there may be adverse reactions because of hypersensitivity to cyanoacrylates themselves or formaldehyde, one of the starting materials used for preparing cyanoacrylate adhesives.

The first cyanoacrylates used as tissue adhesives included the short chain cyanoacrylates, commonly referred to as Super Glues™, were associated with severe acute and chronic inflammatory reactions. Subsequently, longer chain cyanoacrylates, including butyl and octyl cyanoacrylates have gained acceptance. While butyl cyanoacrylates provide effective closure of simple superficial lacerations and incisions, they are toxic when introduced into vascular areas and exhibit low tensile strength and high brittleness.

Octyl cyanoacrylates have proved to be superior adhesives for wound closure, demonstrating greater tensile strength than the butyl cyanoacrylates, and are remarkably nontoxic when used for skin wound closure, but may be toxic if allowed to enter the wound. Octyl cyanoacrylate has been approved by the FDA for use as a tissue adhesive. However, there are problems associated with its use, including a higher incidence of wound infection when compared to suturing as a wound closure method. Also, blood and body fluids trigger premature polymerization of the cyanoacrylate, resulting in an unsightly plasticized mass with very little skin bonding. It is also difficult to keep adhesive out of the wound. The polymerization reaction is exothermic, and the generated heat can result in patient discomfort. Octyl cyanoacrylates may have a low viscosity, causing them to run into undesirable areas or into the wound. For example, cyanoacrylates running into the eye can result in tarsorrhaphy (lid fusion) or corneal injury.

SUMMARY OF THE INVENTION

There is a need in the art of wound closure for a device and a method of applying an adhesive with greater ease and with improved wound healing and to prevent the adhesive from running into the wound or inadvertently into the eye, nose, mouth, or other areas.

In a first embodiment, a wound approximation device is provided, the device including a resilient sheet and an opening, wherein the opening is of a sufficient size such that it surrounds a skin wound and exposes a margin of skin surrounding the wound when the resilient sheet in a stretched form is placed against the skin, and wherein a portion of the resilient sheet adjacent to the opening and opposite to a side of the resilient sheet to be placed against the skin includes a substance which does not form a strong bond with a wound-sealing adhesive used to seal the wound.

In various aspects of the first embodiment, the resilient sheet includes an elastomer, a vinyl sheet, or a urethane sheet. The portion of the resilient sheet adjacent to the opening and opposite to a side of the resilient sheet to be placed against the skin may include a vinyl, or a urethane. The portion of the resilient sheet to be placed against the skin may include a backing adhesive, for example, a pressure sensitive adhesive, such as a butyl acrylate. The wound sealing adhesive may include a cyanoacrylate.

In a second embodiment, a method of sealing a wound is provided, the method including the steps of: providing a wound approximation device, the device including a resilient sheet and an opening; applying tension to the resilient sheet whereby the opening is enlarged to a sufficient size such that it may surround a skin wound and expose a margin of skin surrounding the wound; pressing the resilient sheet under tension against the skin to form a bond to the skin, such that the opening surrounds the skin wound and exposes a margin of skin surrounding the wound; and releasing the tension in the resilient sheet, whereby the wound is approximated.

In various aspects of the second embodiment, the method may further include the step of debriding the approximated wound, irrigating the approximated wound, disinfecting the approximated wound, or sealing the approximated wound. When the method includes the further step of sealing the approximated wound, the step may include suturing the approximated wound, stapling the approximated wound, or applying a wound sealing adhesive to the approximated wound.

In another aspect of the second embodiment, the method further includes the step of removing the wound approximation device from the skin, wherein said step is conducted after the step of sealing the approximated wound. The resilient sheet may include a urethane sheet, and the step of sealing the approximated wound may include applying a cyanoacrylate adhesive to the approximated wound.

BRIEF DESCRIPTION OF THE DRAWINGS

FIG. 3 provides illustrations depicting the use of the wound approximation device.

DETAILED DESCRIPTION OF THE PREFERRED EMBODIMENTS

Introduction

Figure 1:
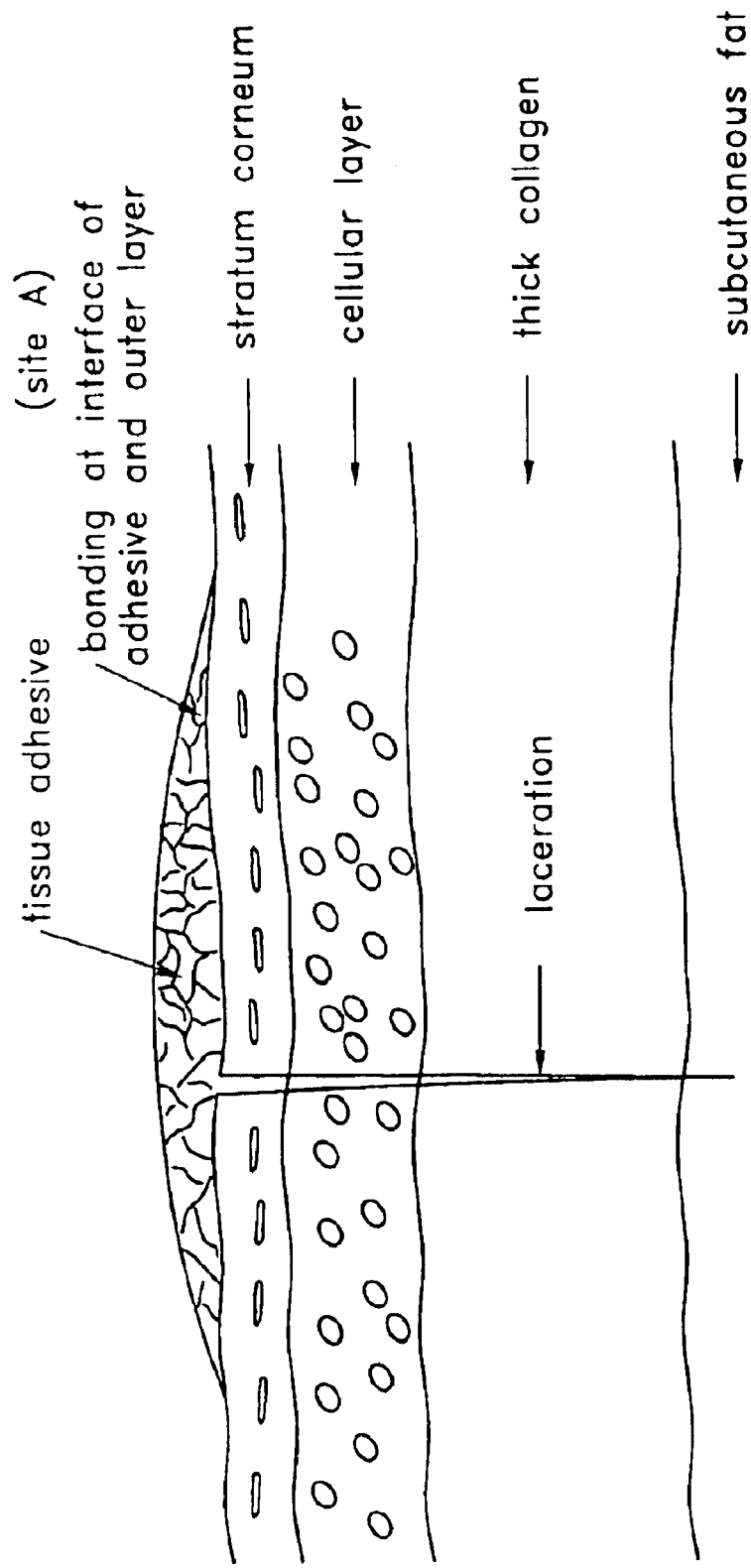
FIG. 1 provides a diagram depicting a skin wound laceration and the position of a tissue adhesive with respect to the various layers of the skin, including the stratum corneum, cellular layer, thick collagen layer, and subcutaneous fat.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Minimally Invasive Surgery (MIS) surgery has lessened suffering of patients. Medical cyanoacrylate adhesives have been successfully used for effectively sealing the wounds acquired during such surgery, as well as for sealing other wounds such as lacerations.

A device is provided for use in applying an adhesive, for example, a cyanoacrylate medical adhesive, to skin in order to seal a wound or laceration. The device includes a sheet of resilient material provided with an opening. The opening is typically in the form of a slit in the resilient material, although in certain embodiments the opening may take a different form, e.g., a circle, rectangle or square, elipse, lens-shape, or the like. The sheet may be stretched, applied to the area of skin surrounding the wound, then the tension released, thereby approximating the wound. An adhesive is then applied to the approximated wound. The surfaces of the sheet material surrounding the wound on the side of the sheet opposite the skin preferably include a material that does not form a strong bond with the adhesive, so as to facilitate removal of the sheet after application of the adhesive.

Cyanoacrylate Adhesives

The adhesives of the preferred embodiments include polymers of 2-cyanoacrylic esters, more commonly referred to as cyanoacrylates. Cyanoacrylates are hard glass resins that exhibit excellent adhesion to high energy surfaces, such as skin, but do not form strong bonds with low energy materials, e.g., polyolefins, polytetrafluoroethylene (marketed under the name Teflon™), and polyvinylchloride (commonly referred to as vinyl). Cyanoacrylate polymers are spontaneously formed when their liquid monomers are placed between two closely fitting surfaces. The excellent adhesive properties of cyanoacrylate polymers arises from the electron-withdrawing characteristics of the groups adjacent to the polymerizable double bond, which accounts for both the extremely high reactivity or cure rate, and their polar nature, which enables the polymers to adhere tenaciously to many diverse substrates.

Cyanoacrylate Monomer Chemistry

Some of the more common cyanoacrylate monomers include, but are not limited to, the ethyl, methyl, isopropyl, allyl, n-butyl, isobutyl, methoxyethyl, ethoxyethyl, and octyl esters. Cyanoacrylate adhesives are manufactured and marketed worldwide by various companies including Loctite, a Henkel Company, of Rocky Hill, Conn., SAFE-T-LOC International Corporation of Lombard, Ill., SUR-LOK Corporation of Walworth, Wis., and Elmers Products, of Columbus, Ohio, the manufacturer of the well-known Krazy Glue™. The ability of cyanoacrylates to rapidly cure and bond to skin makes them particularly well suited for use as medical adhesives. Cyanoacrylate adhesives suitable for use as medical adhesives include octyl 2-cyanoacrylate marketed as Dermabond™ topical skin adhesive by Ethicon, Inc., a Johnson & Johnson Company, of Somerville, N.J., and butyl cyanoacrylate marketed as Vetbond™ by World Precision Instruments, Inc. of Sarasota, Fla.

The 2-cyanoacrylic ester monomers are all thin, water-clear liquids with viscosities of 1–3 mPa. Only a few of the many esters that have been prepared and characterized are of any significant commercial interest. Methyl and ethyl cyanoacrylates are most commonly used for industrial adhesives. Cyanoacrylate adhesives for medical and veterinary use generally include the longer alkyl chain cyanoacryates, including the butyl and octyl esters.

The base monomers are generally too thin for convenient use and therefore are generally formulated with stabilizers, thickeners, and property-modifying additives. The viscosities of such cyanoacrylate adhesives can range from that of the base monomer to thixotropic gels. The alkyl esters are characterized by sharp, lacrimatory, faintly sweet odors, while alkoxyalkyl esters are nearly odor free, but less effective adhesives.

Bond Formation

Cyanoacrylate liquid monomers polymerize nearly instantaneously via an anionic mechanism when brought into contact with any weakly basic or alkali surface. Even the presence of a weakly basic substance such as adsorbed surface moisture is adequate to initiate the curing reaction. The curing reaction proceeds until all available monomer has reacted or until it is terminated by an acidic species. The time of fixture for cyanoacrylate occurs within several seconds on strongly catalytic surfaces such as skin to several minutes on noncatalytic surfaces. Surface accelerators or additives enhancing the curing rate may be used to decrease the time of fixture on noncatalytic surfaces. However, such accelerators and additives are generally not preferred for use in bonding skin due to the catalytic nature of the skin surface. The basic polymerization reaction includes the following initiation, propagation, and termination steps:

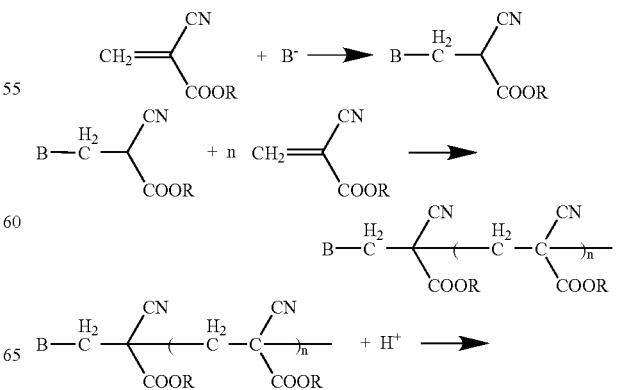

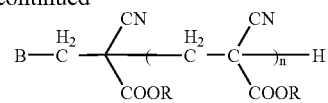

Cyanoacrylate Adhesive Formulations

Cyanoacrylate adhesives are soluble in N-methylpyrrolidone, N,N-dimethylformamide, and nitromethane. Cured cyanoacrylates are hard, clear, and glassy thermoplastic resins with high tensile strengths, but tend to be brittle and have only low to moderate impact and peel strengths. Elastomeric materials may be dissolved in cyanoacrylate adhesive formulations to yield a cured adhesive of greater flexibility and toughness. The longer alkyl chain esters generally have longer cure rates, reduced tensile and tensile shear strength and hardness compared to the shorter alkyl chain esters. The longer alkyl chain esters also exhibit reduced glass-transition temperatures ($T_g$) and adhesive bond service temperature when compared to the shorter alkyl chain esters.

Although the alkyl cyanoacrylate esters are the most common cyanoacrylate adhesives, in certain embodiments it may be preferred to use a cyanoacrylate ester adhesive other than an alkyl ester. For example, allyl esters, which may cross-link by a free-radical mechanism through the allyl group, may be used in applications wherein increased thermal resistance is desirable. Alkoxyalkyl esters may be used in those applications where reduced odor is desirable and wherein a slightly reduced adhesive performance is acceptable.

Cyanoacrylate adhesives are prepared via the Knoevenagel condensation reaction, in which the corresponding alkyl cyanoacetate reacts with formaldehyde in the presence of a basic catalyst to form a low molecular weight polymer. The polymer slurry is acidified and the water is removed. The polymer is cracked and redistilled at a high temperature into a suitable stabilizer combination to prevent premature repolymerization. Strong protonic or Lewis acids are normally used in combination with small amounts of a free-radical stabilizer.

Adhesives formulated from the 2-cyanoacrylic esters typically contain stabilizers and thickeners, and may also contain tougheners, colorants, and other special property-enhancing additives. Both anionic and free-radical stabilizers are required, since the monomer will polymerize via both mechanisms. Although the anionic polymerization mechanism depicted above is the predominant reaction, the monomer will undergo free radical polymerization under prolonged exposure to heat or light. To extend the usable shelf life of cyanoacrylate adhesive formulations, free-radical stabilizers such as quinones or hindered phenols are commonly added to the formulations. Anionic inhibitors such as nitric oxide may also be added. Such anionic inhibitors alter the viscosity and polymerization rate, thereby minimizing the risk of inadvertent spillage and facilitating application.

Both the liquid and cured cyanoacrylates support combustion, and highly exothermic polymerization can occur from direct addition of catalytic substances such as water, alcohols, and bases such as amines, ammonia, or caustics, or from contamination with surface activators.

Cyanoacrylate Adhesives for Medical Uses

Cyanoacrylate adhesives will rapidly bond to skin because of the presence of moisture and protein in the skin. Octyl cyanoacrylates are the most widely used cyanoacrylate adhesive for tissue sealing. When bonding to tissue, octyl cyanoacrylates are four times stronger and less toxic than butyl cyanoacrylate. However, butyl cyanoacrylate is sometimes preferred for sealing deeper lacerations because it breaks down more easily and can be absorbed by the tissue more quickly than octyl cyanoacrylate.

The 2-cyanoacrylic esters have sharp, pungent odors and are lacrimators, even at very low concentrations. These esters can be irritating to the nose, throat, and eye at concentrations as low as 3 ppm. Good ventilation when using the adhesives is essential, and contact with the eye or other sensitive body parts is to be avoided when using cyanoacrylate adhesives for wound sealing. The cured 2-cyanoacrylic ester polymers are relatively nontoxic, making them suitable for medical use. While mild skin irritation may be observed, there is no evidence of sensitization or absorption of the cyanoacrylate adhesives through the skin.

Wound Approximation Device and Method for Sealing Skin Wounds

Cyanoacrylate adhesives, or other medical adhesives as are known in the art, may be used in conjunction with a tissue closure device that expediently allows a firm approximation of skin wound edges and prevents body fluids (e.g., tears, sweat, blood) from contaminating the wound. The device includes a stretched sheet with one side adherent to the skin that is applied to surround the laceration. When applied in a stretched state then the tension released, the device controls about the wound, thus holding the wound edges together. The sheet forms a dam that prevents body fluids from contaminating the wound and also prevents the cyanoacrylate adhesive from entering critical structures adjacent to the wound, e.g., the eye, nose, or mouth.

A device to gain wound approximation and insulation from contamination or inadvertent spread of adhesive agents is provided. The wound approximation device includes a resilient material provided with an opening. The opening is of suitable size and shape such that when the resilient material is stretched under tension and positioned on the skin, the opening surrounds the wound to be approximated. After the resilient material is placed on the skin such that the opening surrounds the wound to be approximated, the tension is released and the resilient material contracts. When the resilient material contracts, the wound is approximated. After approximation is achieved, the wound may be subject to treatment, including, but not limited to debridement, irrigation, disinfection, wound sealing or closing, and the like. Closing the wound may be accomplished by use of adhesives, suturing, stapling, laser tissue welding, or other accepted procedures known to those of skill in the art.

Resilient Material

The wound approximation device of preferred embodiments includes an elastic sheet, a stretchable woven or nonwoven fabric, or any other suitable resilient material that may be stretched then draped around the wound. Suitable resilient materials are preferably stretchable in any direction. However, in certain embodiments it may be preferred or acceptable to use a resilient material that is stretchable in only one direction, e.g., longitudinally stretchable. Suitable resilient materials are generally capable of a measured maximum extension of at least about 30% of their relaxed length, preferably at least about 40% or 50% of their relaxed length, more preferably at least about 60%, 70%, 80%, or 90% of their relaxed length, and most preferably at least about 100%, 150%, 200%, 250%, 300%, 400%, 500% or more of their relaxed length. However, in certain embodiments it may be desirable to use a material capable of a measured maximum extension of less than about 30% of its relaxed length.

In preferred embodiments, the resilient material includes one or more sheets of elastomers. Elastomers are polymers possessing elastic properties. Preferred elastomers include, but are not limited to, natural and synthetic rubbers such as styrene-butadiene rubbers, butyl rubbers, acrylonitrile-butadiene rubbers, polysulfide rubbers, latex, neoprene, polyurethanes, polyacrylate elastomers, silicone elastomers, fluoroelastomers, polyolefins such as ethylene-propylene elastomers, and polyvinyl chlorides. A single elastomer may be used, or a mixture or combination of two or more elastomers may be used. In general, it is preferred that the elastomeric material exhibit an elongation of about 100% at 2,800 psi (19.3 MPa). However, in certain embodiments an elastomeric material exhibiting 100% elongation at greater than or less than 2,800 psi may be preferred.

Other suitable elastic materials include resilient stretchable fabrics. Such fabrics may include woven or nonwoven fibers of the elastomeric materials described above. An example of a suitable fiber that may be used in resilient stretchable fabrics is Lycra™ a stretchy fiber made from lightweight polyurethane. Lycra™ is available from DuPont Corp. of Wilmington, Del.

While solid sheets of elastomeric material are generally preferred, in certain embodiments it may be preferred to use a sheet other than a solid sheet, e.g., a perforated sheet. A perforated sheet may be preferred for applications wherein the wound approximation device is left in place on the skin for an extended period of time, the perforations permitting air circulation to the skin under the perforations.

In preferred embodiments, the elastic material comprises polyvinylchloride (commonly referred to as vinyl) or polyurethane sheeting. A polyurethane material suitable for use in preferred embodiments is marketed under the tradename DuBan® Cohesive Elastic Bandage by Dumex U.S.A. of Marietta, Ga. DuBan is a latex-free cohesive elastic bandage that adheres to itself, but not to the skin or hair. It conforms to body contours while offering controlled compression, and is lightweight and water resistant.

Other materials that may be suitable for use in various preferred embodiments are commercially available from CT Biomaterials, a Division of CardioTech International, Inc. of Wyburn, Mass. These materials are marketed under the tradenames ChronoFlex® C, ChronoFlex® AR, ChronoThane® P, and ChronoPrene™.

ChronoFlex® C is a family of polycarbonate aromatic biodurable thermoplastic polyurethane elastomers developed by CT Biomaterials, a Division of CardioTech International, Inc. of Wyburn, Mass. Typical properties for ChronoFlex® C materials having various hardnesses is provided in Table 1 below.

TABLE 1

Physical Properties of ChronoFlex ® C Polymers

| Properties | ASTM Procedure | Typical Values | | |
|---|---|---|---|---|
| Hardness (Shore Durometer) | ASTM D-2240 | 80 A | 55 D | 75 D |
| Appearance | Visual | Clear to slightly cloudy | Clear to slightly cloudy | Clear to slightly cloudy |
| Ultimate Tensile Strength (psi) | ASTM D-638 | 5500–6500 | 6000–7500 | 7000–8000 |
| Ultimate Tensile Strain (%) | ASTM D-638 | 400–490 | 365–440 | 255–320 |
| 100% Secant Modulus (psi) | ASTM D-638 | 770–1250 | 1850–2200 | 5300–5700 |
| 300% Secant Modulus (psi) | ASTM D-638 | 700–1400 | 1700–2000 | 2700–3200 |
| Flexural Strength (psi) | ASTM D-790 | 350 | 550 | 10,000 |
| Flexural Modulus (psi) | ASTM D-790 | 5500 | 9300 | 300,000 |
| Melt Index (g/10 min) 210° C.; 2.17 Kg | ASTM D-1238 | 8 | 5 | 3 |
| Vicat Softening Point (° F./° C.) | ASTM D-1525 | 160/70 | 180/80 | — |
| Water Absorption | ASTM D-5170 | 1.2 | 1.0 | 0.8 |
| Dielectric Strength (volts/Mil) | ASTM D-149 | 360 | 520 | 420 |
| Specific Gravity | ASTM D-792 | 1.2 | 1.2 | 1.2 |
| Coefficient of Friction (Kinetic) | ASTM D-1894 | 1.5 | 0.8 | 0.64 |
| Abrasion Resistance (% loss at 1000 cycles) | ASTM D-1044 | 0.008 | 0.035 | 0.053 |
| Melt Process. Temp. (° F./° C.) | | 375–430/190–220 | | |
| Recommended Sterilization Method | | Gamma; E-Beam; ethylene oxide | | |
| Class VI Biocompatibility Test | U.S.P. XXII | Pass | Pass | Pass |

ChronoFlex® AR is a solution-grade, segmented, aromatic, polycarbonate-based polyurethane elastomer. Films prepared from ChronoFlex® AR pass or exceed all requirements specified in the USP Class VI biocompatibility tests. Typical physical properties of ChronoFlex® AR films are provided in Table 2 below.

TABLE 2

Physical Properties of ChronoFlex ® AR Polymers

| | |
|---|---|
| Durometer, (Shore) ASTM D-2240 | 75 A |
| Tensile Strength ASTM D-412 | 7500 psi |
| Elongation ASTM D-412 | 500% |

ChronoThane™ P is a family of aromatic ether-based polyurethane elastomers. It has a low coefficient of friction, low extractables, dimensional stability, gama sterilizable, chemical inertness, and biodurability, and easy thermoplastic processibility. Typical physical properties of ChronoThane P-80 A are provided in Table 3 below.

TABLE 3

| Physical Properties of ChronoThane ® P Polymers | |
| --- | --- |
| Durometer (Shore) ASTM D-2240 | 80 A |
| Tensile Strength ASTM D-412 | 5100 psi |
| Elongation ASTM D-412 | 550% |
| Modulus @ 100% Elongation | 850 psi |
| Modulus @ 300% Elongation | 1750 psi |
| Tear Strength Die "C" ASTM D-624 | 420 pli |
| Vicat Softening ASTM D-1525 | 185° F. |
| Flexural Modulus ASTM D-790 | 15000 psi |

ChronoPrene™ is based on styrenic olefinic rubber and hydrogenated isoprene. ChronoPrene™ contains polypropylene as a reinforcing agent and mineral oil as a plasticizer and processing aid. Physical properties of ChronoThane® P Polymers are provided in Table 4 below.

TABLE 4

| Physical Properties of ChronoThane ® P Polymers | | |
| --- | --- | --- |
| Hardness-Shore A ASTM D2240 (3 sec.) | 25 A | 40 A |
| Specific Gravity | 0.87 | 0.90 |
| Tensile Strength (psi) (ASTM D412) | 600 | 700 |
| Elongation (ASTM D412) | 600% | 500% |
| Color | Translucent | Translucent |

While vinyl or polyurethane sheeting is preferred for certain embodiments, other suitable elastic material may preferred for other embodiments. Such elastic materials are well known in the art.

The wound approximation device may include a single layer of resilient material, or two or more layers of resilient material bonded together. The layers of resilient material may include the same material, for example, multiple layers of vinyl sheeting. Such a configuration provides flexibility in preparing wound approximation devices of a wide range of thicknesses using a single thickness of sheeting as a starting material. Alternatively, the resilient material may include two different materials, for example, a layer of vinyl sheeting bonded to a stretchable woven or nonwoven fabric. Such a configuration may lend greater structural integrity to the resilient material, thereby preventing or minimizing inadvertent enlarging of the opening by tearing when tension is applied to the wound approximation device.

The resilient material may be provided with one or more coatings, if desired. Such coatings may assist in forming a bond between the skin and the wound approximation device, or may prevent undesired adhesion of materials, e.g., adhesives, to the wound approximation device.

Pressure Sensitive Adhesive

To ensure that the skin surrounding the wound remains affixed to the resilient material after the stretching of the resilient material is relaxed, it is preferred that the side of the resilient material adjacent to the skin incorporates a suitable adhesive. Although any adhesive suitable for forming a bond with skin may be used, it is generally preferred to use a pressure sensitive adhesive. Pressure sensitive adhesives are generally defined as adhesives that adhere to a substrate when a light pressure is applied but leave no residue when removed. Pressure sensitive adhesives include, but are not limited to, solvent in solution adhesives, hot melt adhesives, aqueous emulsion adhesives, calenderable adhesive, and radiation curable adhesives. Solution adhesives are preferred for most uses because of their ease of application and versatility. Hot melt adhesives are typically based on resin-tackified block copolymers. Aqueous emulsion adhesives include those prepared using acrylic copolymers, butadiene styrene copolymers, and natural rubber latex. Radiation curable adhesives typically consist of acrylic oligomers and monomers, which cure to form a pressure sensitive adhesive upon exposure to ultraviolet lights.

The most commonly used elastomers in pressure sensitive adhesives include natural rubbers, styrene-butadiene latexes, polyisobutylene, butyl rubbers, acrylics, and silicones. In preferred embodiments, acrylic polymer or silicone based pressure sensitive adhesives are used. Acrylic polymers generally have a low level of allergenicity, are cleanly removable from skin, possess a low odor, and exhibit low rates of mechanical and chemical irritation. Medical grade silicone pressure sensitive adhesives are preferred for their biocompatibility.

Amongst the factors that influence the suitability for a pressure sensitive adhesive for use in the wound sealing devices of preferred embodiments are the absence of skin irritating components, sufficient cohesive strength such that the adhesive may be cleanly removed from the skin, ability to accommodate skin movement without excessive mechanical skin irritation, and good resistance to body fluids.

In preferred embodiments, the pressure sensitive adhesive comprises a butyl acrylate. Such adhesives are used as the pressure sensitive adhesive in the DuBan® Cohesive Elastic Bandage described above. While butyl acrylate pressure sensitive adhesives are generally preferred for many application, any pressure sensitive adhesive suitable for bonding skin may be used. Such pressure sensitive adhesives are well known in the art.

In certain embodiments, the portion of the wound sealing device in contact with skin may form a sufficient bond (for example, by friction) with the skin such that an adhesive, such as a pressure sensitive adhesive, is not necessary. However, for ease of use and to ensure that the skin remains in fixed position after the stretching is relaxed, it is generally preferred that a pressure sensitive adhesive is used.

Low Surface Energy Coating

In certain embodiments, the wound approximation device may be used to approximate a wound prior to closing the wound using an adhesive, for example, a cyanoacrylate adhesive. In such applications, it is desirable that the cyanoacrylate or other adhesive adheres only to the skin, and not to the wound approximation device so that the wound approximation device may be easily removed from the skin after the wound is closed.

Cyanoacrylate adhesives do not achieve very high bond strength on low surface energy polymers. Surface energy is a relative phenomenon, so to gauge the effects of surface energy on adhesion, the surface energy of a liquid must be compared to that of a solid surface. A liquid possessing a lower surface energy than the solid surface will spontaneously wet out the solid surface. Conversely, a liquid possessing a higher surface energy than the solid surface will bead up on the surface instead of wetting out. Wet out generally refers to how well a liquid flows and intimately covers a surface. Maximum adhesion develops when the adhesive thoroughly wets out the surface to be bonded. The greater the wet out, the better the surface coverage and the greater the attractive forces between the adhesive and the solid surface. Surfaces with low surface energy do not readily form bonds because they are more difficult to wet with the adhesive.

Polymers having a low surface energy when compared to cyanoacrylate adhesives are well known in the art, and include, for example, vinyls, polyolefins, fluoropolymers, and certain silicones. Low surface energy polymers suitable for use in preferred embodiments include, but are not limited to, polyvinylchloride, polypropylene, polyethylene, polytetrafluoroethylene.

In preferred embodiments wherein the wound approximation device is used in conjunction with a cyanoacrylate adhesive, the resilient material is made up of a low surface energy polymer. Alternatively, a portion of the resilient material adjacent to the opening surrounding the wound may be coated with a low surface energy material. In other embodiments, one or more surfaces of the resilient material are completely coated with a low surface energy material. Alternatively, a composite including two or more layers of different materials may be prepared, wherein one of the layers is the resilient material and another layer is a low surface energy material. The two layers may then be bonded using any suitable method, e.g., adhesives such as pressure sensitive adhesives, hot melt adhesives, curable adhesives, application of heat or pressure such as in lamination, physical attachment through the use of stitching, studs, or other fasteners, and the like.

When the resilient material is a sheet of a low surface energy material, such as vinyl, and a pressure sensitive adhesive is used to adhere the wound approximation device to the skin, it may be desirable to subject the surface of the sheet bearing the pressure sensitive adhesive to a pretreatment or priming prior to application of the pressure sensitive adhesive so as to improve the bonding of the pressure sensitive adhesive to the sheet. Alternatively, a pressure sensitive adhesive specifically formulated for use with a low surface energy material may be selected. Certain acrylic-based pressure sensitive adhesives are especially preferred for use with low surface energy materials.

Other coatings may be preferred if adhesives other than cyanoacrylates are used. When such other adhesives are used, a coating or an uncoated sheet should be selected such that the adhesive does not form a strong bond with the sheet.

The Opening

The wound approximation device is provided with at least one opening. A wound approximation device may be provided with an opening preformed. Alternatively, the opening may be formed in the continuous sheet prior to use in view of the wound to be sealed, the size and the shape of the opening configured to match that of the wound. In certain embodiments, it may be desirable to include more than one opening. For example, two wounds adjacent to each other may be closed simultaneously using a wound approximation device having two openings. Alternatively, if the wound is particularly long, it may be desirable to have a series of openings separated by small bridges of the material of the sheet, or a larger opening wherein opposite sides of the opening are secured together at a series of points along the opening, e.g., by stitching or appropriate fasteners. Such a configuration may enable the center portion of a long wound to be better approximated than if a long, unbroken opening is provided. The maximum size of an opening that provides satisfactory wound approximation may differ depending upon the nature of the resilient material used. Certain resilient materials may be preferred for closing small wounds, whereas other materials may be preferred for approximating larger wounds. Vinyl sheeting is generally preferred as providing satisfactory results for a wide range of wound sizes. The wound approximation device is preferably used to approximate wounds up to about 3 to 4 cm in length. However, in certain embodiments the wound approximation device may be used to approximate wounds longer than about 3 to 4 cm.

The Wound Approximation Device

The wound approximation device may be provided in the form of a sheet of preselected size. Alternatively, a larger sheet of material may be cut or trimmed to provide a wound approximation device of a size and shape appropriate to the wound. The wound approximation device is typically removed from the skin after approximation and sealing of the wound. However, in certain embodiments it may be preferred to leave the wound approximation device in place for an extended period of time. In such applications, it may be preferred to select a pressure sensitive adhesive appropriate for extended contact with the skin, or to include an appropriate medicament, e.g., an antibiotic, an anti-inflammatory composition, or an anesthetic, in the pressure sensitive adhesive.

Wound Approximation and Closure with a Cyanoacrylate Adhesive

Figure 2:
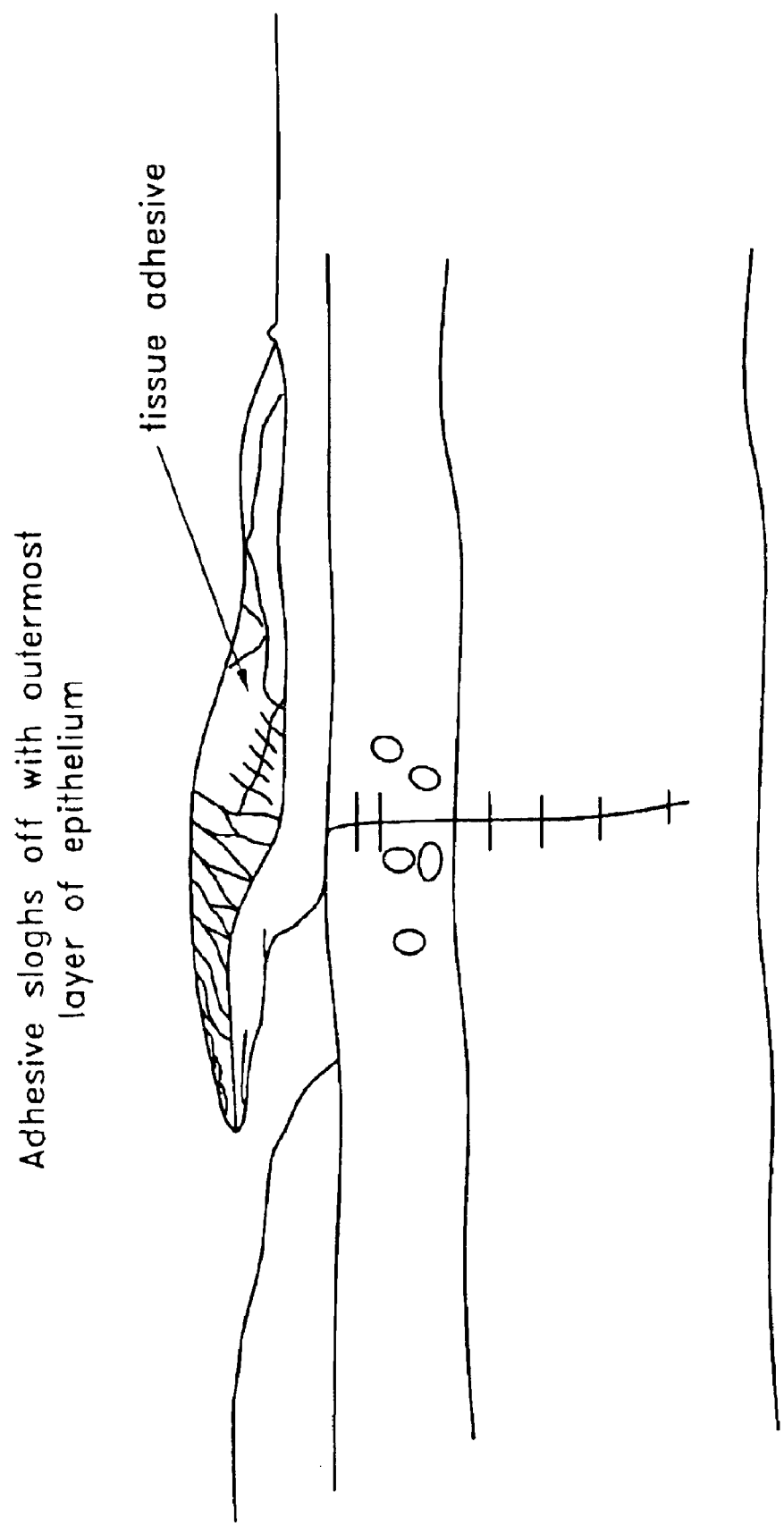
FIG. 2 provides a diagram depicting how an adhesive typically sloughs off with the outermost layer of the stratum corneum.

In a preferred embodiment, the wound approximation device is used to approximate a wound prior to sealing it with a cyanoacrylate adhesive. Illustrated in FIG. 1 is a skin wound laceration and the position of a tissue adhesive with respect to the various layers of the skin, including the stratum corneum, cellular layer, thick collagen layer, and subcutaneous fat. The tissue adhesive bonds to the outer cornified layer of skin. Tissue bonding occurs at site A—the interface between the tissue adhesive and the stratum corneum. FIG. 2 illustrates how the adhesive typically sloughs off with the outermost layer of the stratum corneum, generally from 1–2 weeks after application of the adhesive.

Figure 3A:
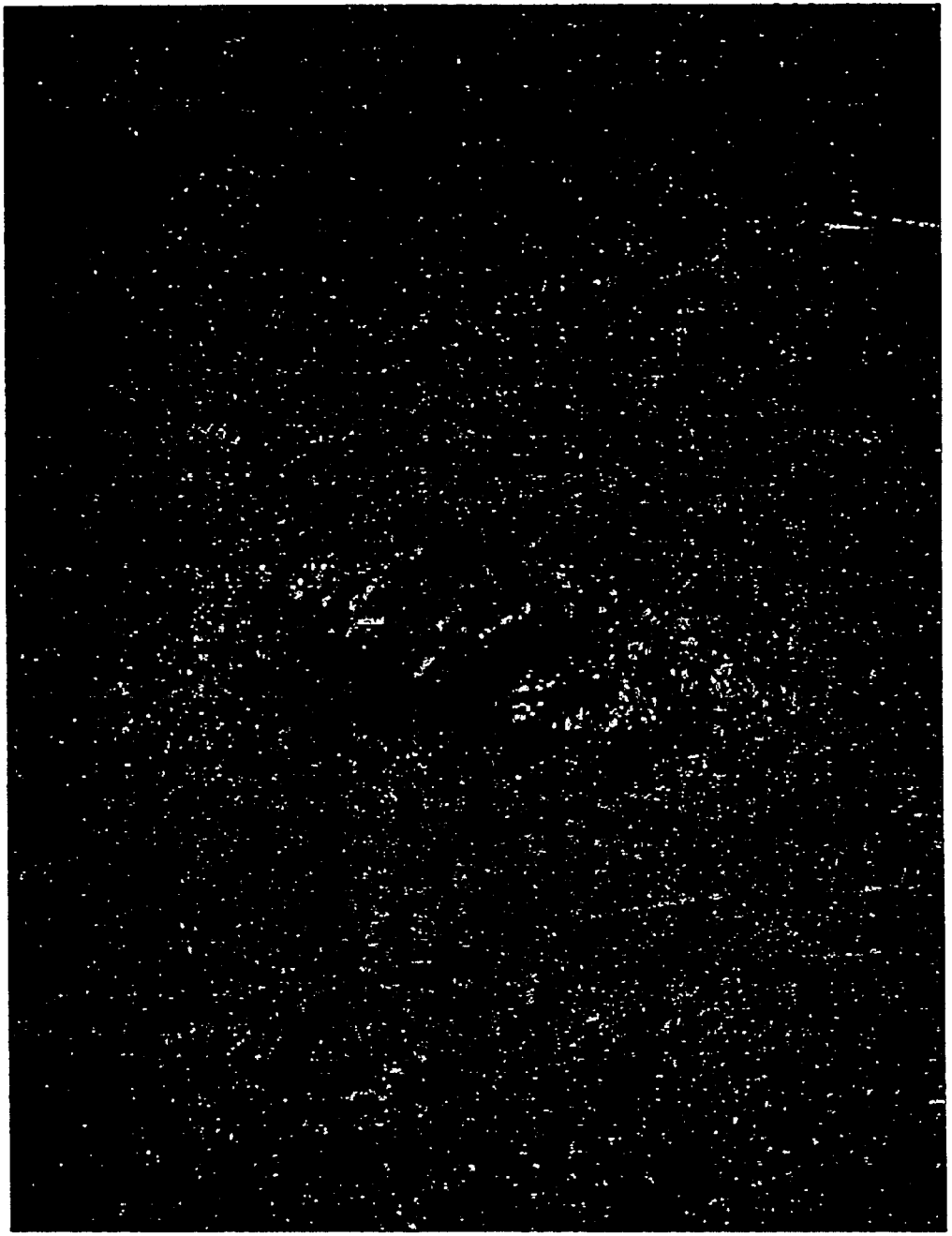
FIG. 3a illustrates a wound.
Figure 3B:
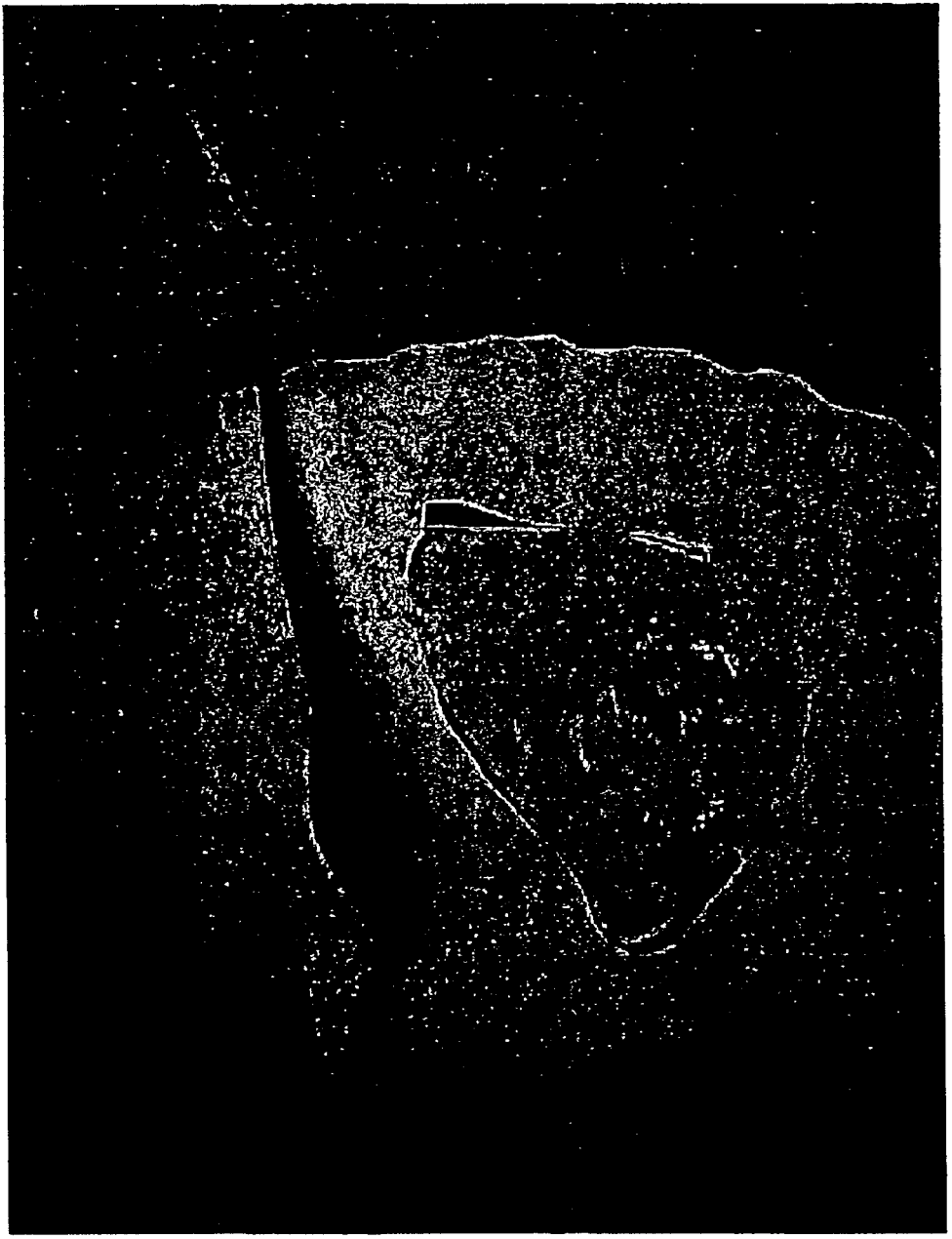
FIG. 3b illustrates the device when stretched under tension to enlarge the opening.
Figure 3C:
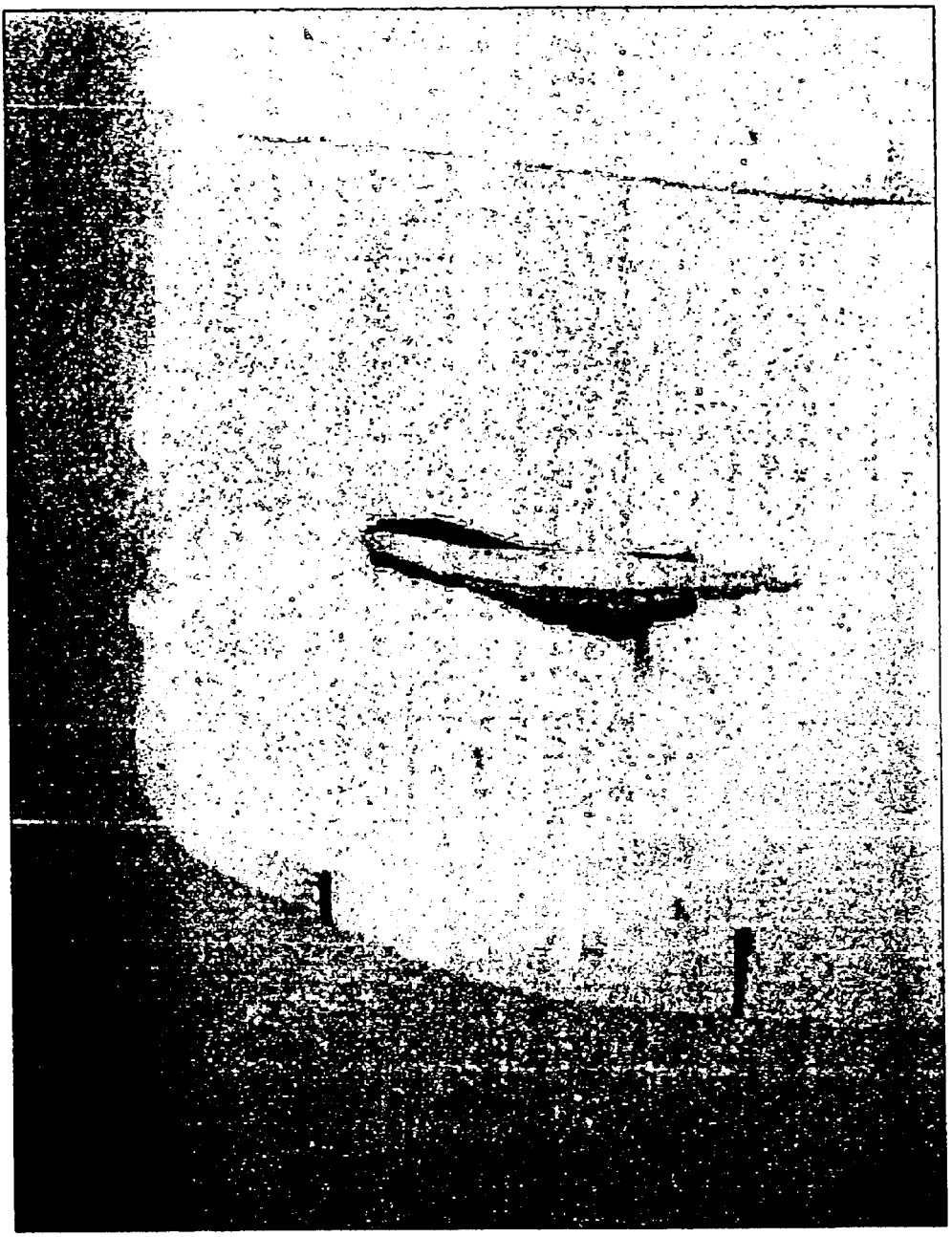
FIG. 3c illustrates the device after application of the stretched device to the wound and release of tension, whereby the wound is approximated.
Figure 3D:
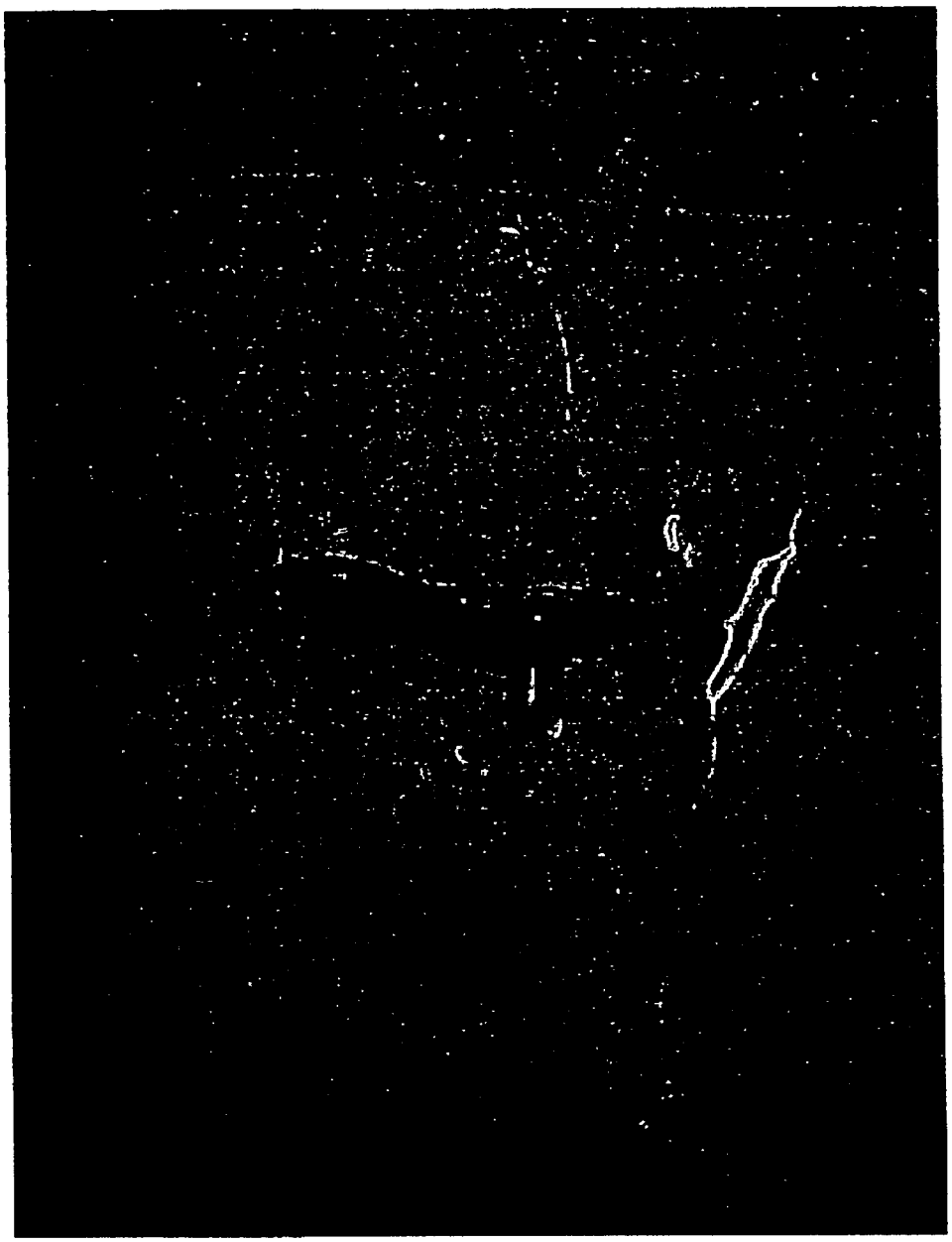
FIG. 3d illustrates the device after application of an adhesive to the approximated wound.

To ensure rapid healing, it is preferred that the adhesive not enter into the wound itself. To minimize entry of the adhesive into the wound, the wound is approximated using the wound approximation device prior to application of the cyanoacrylate adhesive to the wound. FIG. 3 depicts use of the wound approximation device of a preferred embodiment for sealing a wound. FIG. 3a illustrates a laceration approximately 2.5 cm in length on the inner thigh of a pig. FIG. 3b illustrates a wound approximation device of a preferred embodiment, wherein the device includes a DuBan DuBan® Cohesive Elastic Bandage provided with an opening, wherein the side of the bandage to be placed adjacent to the skin is provided with a butyl acrylate pressure sensitive adhesive The sheet is stretched under tension to enlarge the opening, as illustrated in FIG. 3b. Any suitable method may be used to apply the tension, e.g., grasping the edges and pulling them apart, or securing the wound approximation device to an apparatus capable of applying tension to the sheet. The sheet is then pressed to the skin such that the wound is centered in the opening and such that a bond is formed between the pressure sensitive adhesive and the skin. The tension is then released, and the vinyl sheet contracts to approximate the wound, as shown in FIG. 3c. The wound is then sealed by applying a cyanoacrylate adhesive to the skin exposed by the opening, as shown in FIG. 3d. Because vinyl is a low surface energy material when compared to cyanoacrylate, the cyanoacrylate bonds to the skin but does not form an effective bond to the vinyl sheeting. Therefore, after the cyanoacrylate cures, the vinyl sheet may be removed from the skin without substantially disturbing the bond between the cyanoacrylate and the skin.

The above description discloses several methods and materials of the present invention. This invention is susceptible to modifications in the methods and materials, as well as alterations in the fabrication methods and equipment.

Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

Every reference mentioned herein is hereby incorporated by reference in its entirety.

What is claimed is:

1. A wound approximation device, the device comprising:
a cyanoacrylate wound-sealing adhesive; and
a solid resilient sheet comprising an opening, wherein the opening is of a sufficient size such that it surrounds a skin wound and exposes a margin of skin surrounding the wound when the resilient sheet in a stretched form is placed against the skin, wherein the resilient sheet is configured to approximate the wound when allowed to relax into an unstretched form when placed against the skin, and wherein a portion of the resilient sheet adjacent to the opening and opposite to a side of the resilient sheet to be placed against the skin is coated with a low surface energy material which does not form a strong bond with a the cured cyanoacrylate wound-sealing adhesive, such when the cyanoacrylate wound-sealing adhesive is applied through the opening to the margin of skin surrounding the approximated wound so as to seal the wound upon curing, the resilient sheet can be removed from against the skin without disturbing the cured cyanoacrylate adhesive sealing the wound.

2. The wound approximation device of claim 1, wherein the resilient sheet comprises an elastomer.

3. The wound approximation device of claim 1, wherein the resilient sheet comprises a vinyl sheet.

4. The wound approximation device of claim 1, wherein the resilient sheet comprises a urethane sheet.

5. The wound approximation device of claim 1, wherein the portion of the resilient sheet adjacent to the opening and opposite to a side of the resilient sheet to be placed against the skin comprises a vinyl.

6. The wound approximation device of claim 1, wherein the portion of the resilient sheet adjacent to the opening and opposite to a side of the resilient sheet to be placed against the skin comprises a urethane.

7. The wound approximation device of claim 1, wherein a portion of the resilient sheet to be placed against the skin comprises a backing adhesive.

8. The wound approximation device of claim 7, wherein the backing adhesive comprises a pressure sensitive adhesive.

9. The wound approximation device of claim 8, wherein the pressure sensitive adhesive comprises a butyl acrylate.

10. The wound approximation device of claim 1, wherein the cyanoacrylate wound sealing adhesive comprises a butyl cyanoacrylate or an octyl cyanoacrylate.

11. A method of sealing a wound, the method comprising the steps of:
providing a wound approximation device, the device comprising a solid resilient sheet comprising an opening, wherein a portion of the resilient sheet adjacent to the opening and opposite to a side of the resilient sheet to be placed against the skin is coated with a low surface energy material which does not form a strong bond with a cured cyanoacrylate adhesive;
applying tension to the resilient sheet whereby the opening is enlarged to a sufficient size such that it can surround a skin wound and expose a margin of skin surrounding the wound;
pressing the resilient sheet under tension against the skin to form a bond to the skin, such that the opening surrounds the skin wound and exposes a margin of skin surrounding the wound;
releasing the tension in the resilient sheet, whereby the wound is approximated;
applying a cyanoacrylate adhesive through the opening to the margin of skin surrounding the approximated wound;
allowing the cyanoacrylate adhesive to cure, whereby the wound is sealed; and
removing the resilient sheet from against the skin without disturbing the cured cyanoacrylate adhesive sealing the wound.

12. The method of claim 11, further comprising the step of:
debriding the approximated wound.

13. The method of claim 11, further comprising the step of:
irrigating the approximated wound.

14. The method of claim 11, further comprising the step of:
disinfecting the approximated wound.

15. The method of claim 11, further comprising suturing the approximated wound, wherein suturing is conducted before applying a cyanoacrylate adhesive through the opening to the margin of skin surrounding the approximated wound.

16. The method of claim 11, further comprising stapling the approximated wound, wherein stapling is conducted before applying a cyanoacrylate adhesive through the opening to the margin of skin surrounding the approximated wound.

17. The method of claim 11, wherein the resilient sheet comprises a urethane sheet.

18. The method of claim 11, wherein the resilient sheet comprises an elastomer.

19. The method of claim 11, wherein the resilient sheet comprises a vinyl sheet.

20. The method of claim 11, wherein the portion of the resilient sheet adjacent to the opening and opposite to a side of the resilient sheet to be placed against the skin comprises a vinyl.

21. The method of claim 11, wherein the portion of the resilient sheet adjacent to the opening and opposite to a side of the resilient sheet to be placed against the skin comprises a urethane.

22. The method of claim 11, wherein a portion of the resilient sheet to be placed against the skin comprises a backing adhesive.

23. The method of claim 22, wherein the backing adhesive comprises a pressure sensitive adhesive.

24. The method of claim 23, wherein the pressure sensitive adhesive comprises a butyl acrylate.

25. The method of claim 11, wherein the cyanoacrylate adhesive comprises a butyl cyanoacrylate or an octyl cyanoacrylate.

* * * * *